(12) United States Patent
Schorzman et al.

(10) Patent No.: US 7,960,447 B2
(45) Date of Patent: *Jun. 14, 2011

(54) CATIONIC END-CAPPED SILOXANE PREPOLYMER FOR REDUCED CROSS-LINK DENSITY

(75) Inventors: Derek Schorzman, Pittsford, NY (US); Jay Kunzler, Canandaigua, NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 419 days.

This patent is subject to a terminal disclaimer.

(21) Appl. No.: 11/403,393

(22) Filed: Apr. 13, 2006

(65) Prior Publication Data

US 2007/0242215 A1 Oct. 18, 2007

(51) Int. Cl.
*C08F 290/06* (2006.01)
*G02B 1/04* (2006.01)

(52) U.S. Cl. ........ 523/107; 523/106; 623/4.1; 623/5.11; 623/6.11

(58) Field of Classification Search .................. None
See application file for complete search history.

(56) References Cited

U.S. PATENT DOCUMENTS

| | | | |
|---|---|---|---|
| 1,688,453 A | 10/1928 | Demarest et al. | |
| 3,808,179 A | 4/1974 | Gaylord | |
| 3,843,529 A * | 10/1974 | Bertrand ..................... | 508/117 |
| 4,005,024 A | 1/1977 | Rodriguez et al. | |
| 4,006,176 A | 2/1977 | Heckert et al. | |
| 4,153,641 A | 5/1979 | Deichert et al. | |
| 4,185,087 A | 1/1980 | Morlino | |
| 4,189,546 A | 2/1980 | Deichert et al. | |
| 4,259,467 A | 3/1981 | Keogh et al. | |
| 4,260,725 A | 4/1981 | Keogh et al. | |
| 4,388,229 A | 6/1983 | Fu | |
| 4,418,165 A | 11/1983 | Polmanteer et al. | |
| 4,472,327 A | 9/1984 | Neefe | |
| 4,495,361 A | 1/1985 | Friends et al. | |
| 4,533,714 A | 8/1985 | Sebag et al. | |
| 4,633,003 A | 12/1986 | Falcetta et al. | |
| 4,640,941 A | 2/1987 | Park et al. | |
| 4,686,267 A | 8/1987 | Ellis et al. | |
| 4,745,142 A | 5/1988 | Ohwaki et al. | |
| 4,833,225 A | 5/1989 | Schaefer et al. | |
| 4,871,530 A | 10/1989 | Grollier et al. | |
| 4,891,166 A | 1/1990 | Schaefer et al. | |
| 4,910,277 A | 3/1990 | Bambury et al. | |
| 5,006,622 A | 4/1991 | Kunzler et al. | |
| 5,013,459 A | 5/1991 | Gettings et al. | |
| 5,034,461 A | 7/1991 | Lai et al. | |
| 5,039,458 A | 8/1991 | Braatz et al. | |
| 5,070,170 A | 12/1991 | Robertson et al. | |
| 5,070,215 A | 12/1991 | Bambury et al. | |
| 5,128,408 A | 7/1992 | Tanaka et al. | |
| 5,137,448 A | 8/1992 | Dougherty et al. | |
| 5,246,607 A | 9/1993 | Schaefer et al. | |
| 5,260,000 A | 11/1993 | Nandu et al. | |
| 5,321,108 A | 6/1994 | Kunzler et al. | |
| 5,340,583 A | 8/1994 | Dziabo et al. | |
| 5,358,688 A | 10/1994 | Robertson | |
| 5,358,995 A | 10/1994 | Lai et al. | |
| 5,359,104 A | 10/1994 | Higgs et al. | |
| 5,387,105 A | 2/1995 | Dougherty et al. | |
| 5,387,662 A | 2/1995 | Kunzler et al. | |
| 5,393,330 A | 2/1995 | Chen et al. | |
| 5,399,737 A * | 3/1995 | Park et al. ..................... | 556/413 |
| 5,420,324 A | 5/1995 | Lai et al. | |
| 5,424,078 A * | 6/1995 | Dziabo et al. ................ | 424/661 |
| 5,451,617 A | 9/1995 | Lai et al. | |
| 5,451,651 A | 9/1995 | Lai | |
| 5,496,871 A | 3/1996 | Lai et al. | |
| 5,515,117 A | 5/1996 | Dziabo et al. | |
| 5,536,861 A | 7/1996 | Robertson | |
| 5,539,016 A | 7/1996 | Knuzler et al. | |
| 5,594,085 A | 1/1997 | Lai | |
| 5,610,252 A | 3/1997 | Bambury et al. | |
| 5,639,908 A | 6/1997 | Lai | |
| 5,648,515 A | 7/1997 | Lai | |
| 5,707,434 A | 1/1998 | Halloran et al. | |
| 5,710,302 A | 1/1998 | Kunzler et al. | |
| 5,714,557 A | 2/1998 | Kunzler et al. | |
| 5,725,736 A | 3/1998 | Schroeder et al. | |
| 5,776,999 A | 7/1998 | Nicolson et al. | |
| 5,807,956 A | 9/1998 | Czech | |
| 5,830,546 A | 11/1998 | Ehret et al. | |
| 5,844,026 A | 12/1998 | Galbo et al. | |
| 5,908,906 A | 6/1999 | Kunzler et al. | |

(Continued)

FOREIGN PATENT DOCUMENTS

| | | |
|---|---|---|
| EP | 0 017 121 | 4/1983 |
| EP | 0 396 364 | 6/1997 |
| EP | 0 837 103 | 4/1998 |
| EP | 0 837 104 | 4/1998 |
| EP | 1 285 943 | 2/2003 |
| JP | 9183813 | 7/1997 |

OTHER PUBLICATIONS

Odian, George. "Principles of Polymerization," 3rd Edition, John Wiley & Sons, Inc, 1991, p. 200.*
Benjamin, William J., Oxygen Permeability (Dk) of Thirty-Seven Rigid Contact Lens Materials, Optometry and Vision Science, vol. 79, No. 2, Feb. 2002, pp. 103-111.
International Search Report (PCTISA/210) and Written Opinion (PCT/ISA/237) mailed on Aug. 31, 2007.
U.S. Appl. No. 11/341,209, filed Jan. 27, 2006, Schorzman et al.
U.S. Appl. No. 11/480,111, filed Jun. 30, 2006, Schorzman et al.
U.S. Appl. No. 11/480,170, filed Jun. 30, 2006, Schorzman et al.

(Continued)

*Primary Examiner* — Sharmila Landau
*Assistant Examiner* — Rachael E Welter
(74) *Attorney, Agent, or Firm* — Glenn D. Smith; M. Carmen & Associates, PLLC

(57) ABSTRACT

The present invention relates to hydrophilic dicationic siloxane prepolymers with one polymerizable vinyl moiety instead of two polymerizable vinyl moieties, resulting in contact lenses and/or biomedical devices with reduced cross-link density and modulus without detracting from other properties.

22 Claims, No Drawings

U.S. PATENT DOCUMENTS

| | | | |
|---|---|---|---|
| 5,962,548 A | 10/1999 | Vanderlaan et al. | |
| 5,994,488 A | 11/1999 | Yokota et al. | |
| 6,013,711 A | 1/2000 | Lewis et al. | |
| 6,022,836 A | 2/2000 | Dubief et al. | |
| 6,063,888 A | 5/2000 | Yamaguchi et al. | |
| 6,068,929 A | 5/2000 | Dauth et al. | |
| 6,132,705 A | 10/2000 | Schehlmann et al. | |
| 6,166,236 A | 12/2000 | Bambury et al. | |
| 6,242,554 B1 | 6/2001 | Busch et al. | |
| 6,248,803 B1 | 6/2001 | Nakanishi et al. | |
| 6,482,969 B1 | 11/2002 | Helmrick et al. | |
| 6,534,184 B2 | 3/2003 | Knasiak et al. | |
| 6,607,717 B1 | 8/2003 | Johnson et al. | |
| 6,613,755 B2 | 9/2003 | Peterson et al. | |
| 6,630,132 B2 | 10/2003 | Fender et al. | |
| 6,649,722 B2 | 11/2003 | Rosenzweig et al. | |
| 6,706,680 B2 | 3/2004 | Fender et al. | |
| 6,730,767 B2 | 5/2004 | Salamone et al. | |
| 6,787,603 B2 | 9/2004 | Johnson et al. | |
| 6,815,074 B2 | 11/2004 | Aguado et al. | |
| 6,822,016 B2 | 11/2004 | McCabe et al. | |
| 6,849,671 B2 | 2/2005 | Steffen et al. | |
| 6,849,755 B2 | 2/2005 | Ozai et al. | |
| 6,852,793 B2 | 2/2005 | Salamone et al. | |
| 6,893,595 B1 | 5/2005 | Muir et al. | |
| 6,951,894 B1 | 10/2005 | Nicolson et al. | |
| 7,468,397 B2 | 12/2008 | Schorzman et al. | |
| 7,528,208 B2 | 5/2009 | Schorzman et al. | |
| 7,557,231 B2 | 7/2009 | Schorzman et al. | |
| 7,601,766 B2 | 10/2009 | Schorzman et al. | |
| 7,622,512 B2 | 11/2009 | Schorzman et al. | |
| 2003/0108494 A1* | 6/2003 | Fender et al. | 424/59 |
| 2004/0029981 A1 | 2/2004 | Herzig et al. | |
| 2005/0008613 A1 | 1/2005 | Peterson et al. | |
| 2007/0142584 A1* | 6/2007 | Schorzman et al. | 526/264 |
| 2008/0075780 A1* | 3/2008 | Kunzler et al. | 424/487 |
| 2008/0152540 A1* | 6/2008 | Schorzman et al. | 422/40 |

OTHER PUBLICATIONS

U.S. Appl. No. 11/611,508, filed Dec. 15, 2006, Schorzman et al.
U.S. Appl. No. 11/611,512, filed Dec. 15, 2006, Schorzman et al.
U.S. Appl. No. 11/619,211, filed Jan. 3, 2007, Schorzman et al.
U.S. Appl. No. 11/830,885, filed Jul. 31, 2007, Schorzman et al.
U.S. Appl. No. 11/837,049, filed Aug. 10, 2007, Kunzler et al.
U.S. Appl. No. 11/840,650, filed Aug. 17, 2007, Salamone et al.
U.S. Appl. No. 12/018,910, filed Jun. 24, 2008, Stanbro et al.
U.S. Appl. No. 12/313,253, filed Nov. 18, 2008, Schorzman.
U.S. Appl. No. 12/459,778, filed Jul. 8, 2009, Kunzler et al.
U.S. Appl. No. 12/459,779, filed Jul. 8, 2009, Kunzler et al.

* cited by examiner

US 7,960,447 B2

CATIONIC END-CAPPED SILOXANE PREPOLYMER FOR REDUCED CROSS-LINK DENSITY

CROSS-REFERENCE TO RELATED APPLICATIONS

None

FIELD

The present invention relates to polymeric compositions useful in the manufacture of biocompatible medical devices. More particularly, the present invention relates to certain cationic monomers capable of polymerization to form polymeric compositions having desirable physical characteristics useful in the manufacture of ophthalmic devices.

BACKGROUND AND SUMMARY

Polymeric silicon containing materials have been used in a variety of biomedical applications, including, for example, contact lenses and intraocular lenses. Such materials can generally be subdivided into hydrogels and non-hydrogels. Silicon containing hydrogels constitute crosslinked polymeric systems that can absorb and retain water in an equilibrium state and generally have a water content greater than about 5 weight percent and more commonly between about 10 to about 80 weight percent. Such materials are usually prepared by polymerizing a mixture containing at least one silicon containing monomer and at least one hydrophilic monomer. Either the silicon containing monomer or the hydrophilic monomer may function as a crosslinking agent (a crosslinker being defined as a monomer having multiple polymerizable functionalities) or a separate crosslinker may be employed.

Cationic, polymerizable siloxane prepolymers (described in U.S. patent application Ser. No. 11/341,208 filed Jan. 27, 2006, Ser. No. 11/341,209 filed Jan. 27, 2006, 60/756,637 filed Jan. 6, 2006, 60/756,665 filed Jan. 6, 2006, 60/756,638 filed Jan. 6, 2006 and 60/756,982 filed Jan. 6, 2006; each of which is under obligation of assignment to the assignor of this application and each of which is incorporated by reference herein) have desirable properties for use in biomedical and ophthalmic applications including good wetting characteristics, oxygen permeability, and hydrophilicity. However, due to the increased cross-link density that results from using appreciable quantities of these difunctional monomers in device formulations, it is desirable to reduce the cross-link density, and therefore modulus, while retaining other properties.

In this invention, a mono vinyl polymerizable dicationic siloxane is synthesized in which only one, rather than both, of the cationic groups has a vinyl polymerizable moiety. The single vinyl polymerizable moiety results in a non-cross-linking prepolymer that reduces modulus in polymerized monomeric mixtures containing same. Such materials can be synthesized using methods well known in the art and are described using the following formulae:

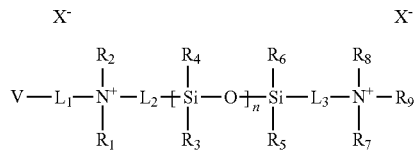

wherein $L_1$, $L_2$ and $L_3$ can individually be the same or different and are selected from the group consisting of urethanes, carbonates, carbamates, carboxyl ureidos, sulfonyls, a straight or branched C1-C30 alkyl group, a C1-C30 fluoroalkyl group, a C1-C20 ester group, an alkyl ether, cycloalkyl ether, cycloalkenyl ether, aryl ether, arylalkyl ether, a polyether containing group, an ureido group, an amide group, an amine group, a substituted or unsubstituted C1-C30 alkoxy group, a substituted or unsubstituted C3-C30 cycloalkyl group, a substituted or unsubstituted C3-C30 cycloalkylalkyl group, a substituted or unsubstituted C3-C30 cycloalkenyl group, a substituted or unsubstituted C5-C30 aryl group, a substituted or unsubstituted C5-C30 arylalkyl group, a substituted or unsubstituted C5-C30 heteroaryl group, a substituted or unsubstituted C3-C30 heterocyclic ring, a substituted or unsubstituted C4-C30 heterocyclolalkyl group, a substituted or unsubstituted C6-C30 heteroarylalkyl group, a C5-C30 fluoroaryl group, or a hydroxyl substituted alkyl ether and combinations thereof; $X^-$ is at least a single charged counter ion; n is an integer from 1 to about 300; $R_1$, $R_2$, $R_3$, $R_4$, $R_5$, $R_6$, $R_7$, $R_8$ and $R_9$ are each independently hydrogen, a straight or branched C1-C30 alkyl group, a C1-C30 fluoroalkyl group, a C1-C20 ester group, an alkyl ether, cycloalkyl ether, cycloalkenyl ether, aryl ether, arylalkyl ether, a polyether containing group, an ureido group, an amide group, an amine group, a substituted or unsubstituted C1-C30 alkoxy group, a substituted or unsubstituted C3-C30 cycloalkyl group, a substituted or unsubstituted C3-C30 cycloalkylalkyl group, a substituted or unsubstituted C3-C30 cycloalkenyl group, a substituted or unsubstituted C5-C30 aryl group, a substituted or unsubstituted C5-C30 arylalkyl group, a substituted or unsubstituted C5-C30 heteroaryl group, a substituted or unsubstituted C3-C30 heterocyclic ring, a substituted or unsubstituted C4-C30 heterocyclolalkyl group, a substituted or unsubstituted C6-C30 heteroarylalkyl group, fluorine, a C5-C30 fluoroaryl group, or a hydroxyl group and V is a polymerizable ethylenically unsaturated organic radical.

Silicon-containing hydrogels combine the beneficial properties of hydrogels with those of silicon-containing polymers (Kunzier and McGee, "Contact Lens Materials", Chemistry & Industry, pp. 651-655, 21 Aug. 1995). Silicon-containing hydrogels as disclosed herein are used to produce a contact lens that combines the high oxygen permeability of polydimethylsiloxane (PDMS) materials with the comfort, wetting and deposit resistance of conventional non-ionic hydrogels. The polymer compositions disclosed herein comprise polymerized silicon containing monomers α-end-capped with an ethylenically unsaturated cationic hydrophilic group.

The present invention provides novel cationic organosilicon-containing monomers which are useful in articles such as biomedical devices including contact lenses.

BRIEF DESCRIPTION OF THE DRAWINGS

None

DETAILED DESCRIPTION

The term "monomer" and like terms as used herein denote relatively low molecular weight compounds that are polymerizable by, for example, free radical polymerization, as well as higher molecular weight compounds also referred to as "prepolymers", "macromonomers", and related terms.

The term "(meth)" as used herein denotes an optional methyl substituent. Accordingly, terms such as "(meth)acrylate" denotes either methacrylate or acrylate, and "(meth) acrylic acid" denotes either methacrylic acid or acrylic acid.

In a first aspect, the invention relates to monomers of formula (I):

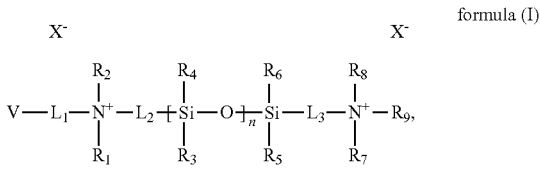

formula (I)

wherein $L_1$, $L_2$ and $L_3$ can individually be the same or different and are selected from the group consisting of urethanes, carbonates, carbamates, carboxyl ureidos, sulfonyls, a straight or branched C1-C30 alkyl group, a C1-C30 fluoroalkyl group, a C1-C20 ester group, an alkyl ether, cycloalkyl ether, cycloalkenyl ether, aryl ether, arylalkyl ether, a polyether containing group, an ureido group, an amide group, an amine group, a substituted or unsubstituted C1-C30 alkoxy group, a substituted or unsubstituted C3-C30 cycloalkyl group, a substituted or unsubstituted C3-C30 cycloalkylalkyl group, a substituted or unsubstituted C3-C30 cycloalkenyl group, a substituted or unsubstituted C5-C30 aryl group, a substituted or unsubstituted C5-C30 arylalkyl group, a substituted or unsubstituted C5-C30 heteroaryl group, a substituted or unsubstituted C3-C30 heterocyclic ring, a substituted or unsubstituted C4-C30 heterocyclolalkyl group, a substituted or unsubstituted C6-C30 heteroarylalkyl group, a C5-C30 fluoroaryl group, or a hydroxyl substituted alkyl ether and combinations thereof.

$X^-$ is at least a single charged counter ion. Examples of single charge counter ions include the group consisting of $Cl^-$, $Br^-$, $I^-$, $CF_3CO_2^-$, $CH_3CO_2^-$, $HCO_3^-$, $CH_3SO_4^-$, p-toluenesulfonate, $HSO_4^-$, $H_2PO_4^-$, $NO_3^-$, and $CH_3CH(OH)CO_2^-$. Examples of dual charged counter ions would include $SO_4^{2-}$, $CO_3^{2-}$ and $HPO_4^{2-}$. Other charged counter ions would be obvious to one of ordinary skill in the art. It should be understood that a residual amount of counter ion may be present in the hydrated product. Therefore, the use of toxic counter ions is to be discouraged. Likewise, it should be understood that, for a singularly charged counter ion, the ratio of counter ion and quaternary siloxanyl will be 1:1. Counter ions of greater negative charge will result in differing ratios based upon the total charge of the counter ion.

n is an integer from 1 to about 300. $R_1$, $R_2$, $R_3$, $R_4$, $R_5$, $R_6$, $R_7$, $R_8$ and $R_9$ are each independently hydrogen, a straight or branched C1-C30 alkyl group, a C1-C30 fluoroalkyl group, a C1-C20 ester group, an alkyl ether, cycloalkyl ether, cycloalkenyl ether, aryl ether, arylalkyl ether, a polyether containing group, an ureido group, an amide group, an amine group, a substituted or unsubstituted C1-C30 alkoxy group, a substituted or unsubstituted C3-C30 cycloalkyl group, a substituted or unsubstituted C3-C30 cycloalkylalkyl group, a substituted or unsubstituted C3-C30 cycloalkenyl group, a substituted or unsubstituted C5-C30 aryl group, a substituted or unsubstituted C5-C30 arylalkyl group, a substituted or unsubstituted C5-C30 heteroaryl group, a substituted or unsubstituted C3-C30 heterocyclic ring, a substituted or unsubstituted C4-C30 heterocyclolalkyl group, a substituted or unsubstituted C6-C30 heteroarylalkyl group, fluorine, a C5-C30 fluoroaryl group, or a hydroxyl group and V is a polymerizable ethylenically unsaturated organic radical.

Representative examples of urethanes for use herein include, by way of example, a secondary amine linked to a carboxyl group which may also be linked to a further group such as an alkyl. Likewise the secondary amine may also be linked to a further group such as an alkyl.

Representative examples of carbonates for use herein include, by way of example, alkyl carbonates, aryl carbonates, and the like.

Representative examples of carbamates, for use herein include, by way of example, alkyl carbamates, aryl carbamates, and the like.

Representative examples of carboxyl ureidos, for use herein include, by way of example, alkyl carboxyl ureidos, aryl carboxyl ureidos, and the like.

Representative examples of sulfonyls for use herein include, by way of example, alkyl sulfonyls, aryl sulfonyls, and the like.

Representative examples of alkyl groups for use herein include, by way of example, a straight or branched hydrocarbon chain radical containing carbon and hydrogen atoms of from 1 to about 18 carbon atoms with or without unsaturation, to the rest of the molecule, e.g., methyl, ethyl, n-propyl, 1-methylethyl (isopropyl), n-butyl, n-pentyl, etc., and the like.

Representative examples of fluoroalkyl groups for use herein include, by way of example, a straight or branched alkyl group as defined above having one or more fluorine atoms attached to the carbon atom, e.g., $-CF_3$, $-CF_2CF_3$, $-CH_2CF_3$, $-CH_2CF_2H$, $-CF_2H$ and the like.

Representative examples of ester groups for use herein include, by way of example, a carboxylic acid ester having one to 20 carbon atoms and the like.

Representative examples of ether or polyether containing groups for use herein include, by way of example, an alkyl ether, cycloalkyl ether, cycloalkenyl ether, aryl ether, arylalkyl ether wherein the alkyl, cycloalkyl, cycloalkylalkyl, cycloalkenyl, aryl, and arylalkyl groups are defined above, e.g., alkylene oxides, poly(alkylene oxide)s such as ethylene oxide, propylene oxide, butylene oxide, poly(ethylene oxide)s, poly(ethylene glycol)s, poly(propylene oxide)s, poly(butylene oxide)s and mixtures or copolymers thereof, an ether or polyether group of the general formula $-R^{10}OR^{11}$, wherein $R^{10}$ is a bond, an alkyl, cycloalkyl or aryl group as defined above and $R^{11}$ is an alkyl, cycloalkyl or aryl group as defined above, e.g., $-CH_2CH_2OC_6H_5$ and $-CH_2CH_2OC_2H_5$, and the like.

Representative examples of amide groups for use herein include, by way of example, an amide of the general formula $-R^{12}C(O)NR^{13}R^{14}$ wherein $R^{12}$, $R^{13}$ and $R^{14}$ are independently $C_1$-$C_{30}$ hydrocarbons, e.g., $R^{12}$ can be alkylene groups, arylene groups, cycloalkylene groups and $R^{13}$ and $R^{14}$ can be alkyl groups, aryl groups, and cycloalkyl groups as defined herein and the like.

Representative examples of amine groups for use herein include, by way of example, an amine of the general formula $-R^{15}NR^{16}R^{17}$ wherein $R^{15}$ is a C2-C30 alkylene, arylene, or cycloalkylene and $R^{16}$ and $R^{17}$ are independently C1-C30 hydrocarbons such as, for example, alkyl groups, aryl groups, or cycloalkyl groups as defined herein, and the like.

Representative examples of an ureido group for use herein include, by way of example, an ureido group having one or more substituents or unsubstituted ureido. The ureido group preferably is an ureido group having 1 to 12 carbon atoms. Examples of the substituents include alkyl groups and aryl groups. Examples of the ureido group include 3-methylureido, 3,3-dimethylureido, and 3-phenylureido.

Representative examples of alkoxy groups for use herein include, by way of example, an alkyl group as defined above attached via oxygen linkage to the rest of the molecule, i.e., of the general formula $-OR^{20}$, wherein $R^{20}$ is an alkyl, cycloalkyl, cycloalkenyl, aryl or an arylalkyl as defined above, e.g., $-OCH_3$, $-OC_2H_5$, or $-OC_6H_5$, and the like.

Representative examples of cycloalkyl groups for use herein include, by way of example, a substituted or unsubstituted non-aromatic mono or multicyclic ring system of about 3 to about 18 carbon atoms such as, for example, cyclopropyl, cyclobutyl, cyclopentyl, cyclohexyl, perhydronapthyl, adamantyl and norbornyl groups bridged cyclic group or spriobicyclic groups, e.g., sprio-(4,4)-non-2-yl and the like, optionally containing one or more heteroatoms, e.g., O and N, and the like.

Representative examples of cycloalkylalkyl groups for use herein include, by way of example, a substituted or unsubstituted cyclic ring-containing radical containing from about 3 to about 18 carbon atoms directly attached to the alkyl group which are then attached to the main structure of the monomer at any carbon from the alkyl group that results in the creation of a stable structure such as, for example, cyclopropylmethyl, cyclobutylethyl, cyclopentylethyl and the like, wherein the cyclic ring can optionally contain one or more heteroatoms, e.g., O and N, and the like.

Representative examples of cycloalkenyl groups for use herein include, by way of example, a substituted or unsubstituted cyclic ring-containing radical containing from about 3 to about 18 carbon atoms with at least one carbon-carbon double bond such as, for example, cyclopropenyl, cyclobutenyl, cyclopentenyl and the like, wherein the cyclic ring can optionally contain one or more heteroatoms, e.g., O and N, and the like.

Representative examples of aryl groups for use herein include, by way of example, a substituted or unsubstituted monoaromatic or polyaromatic radical containing from about 5 to about 25 carbon atoms such as, for example, phenyl, naphthyl, tetrahydronapthyl, indenyl, biphenyl and the like, optionally containing one or more heteroatoms, e.g., O and N, and the like.

Representative examples of arylalkyl groups for use herein include, by way of example, a substituted or unsubstituted aryl group as defined above directly bonded to an alkyl group as defined above, e.g., —$CH_2C_6H_5$, —$C_2H_5C_6H_5$ and the like, wherein the aryl group can optionally contain one or more heteroatoms, e.g., O and N, and the like.

Representative examples of fluoroaryl groups for use herein include, by way of example, an aryl group as defined above having one or more fluorine atoms attached to the aryl group.

Representative examples of heterocyclic ring groups for use herein include, by way of example, a substituted or unsubstituted stable 3 to about 15 membered ring radical, containing carbon atoms and from one to five heteroatoms, e.g., nitrogen, phosphorus, oxygen, sulfur and mixtures thereof. Suitable heterocyclic ring radicals for use herein may be a monocyclic, bicyclic or tricyclic ring system, which may include fused, bridged or spiro ring systems, and the nitrogen, phosphorus, carbon, oxygen or sulfur atoms in the heterocyclic ring radical may be optionally oxidized to various oxidation states. In addition, the nitrogen atom may be optionally quaternized; and the ring radical may be partially or fully saturated (i.e., heteroaromatic or heteroaryl aromatic). Examples of such heterocyclic ring radicals include, but are not limited to, azetidinyl, acridinyl, benzodioxolyl, benzodioxanyl, benzofurnyl, carbazolyl, cinnolinyl, dioxolanyl, indolizinyl, naphthyridinyl, perhydroazepinyl, phenazinyl, phenothiazinyl, phenoxazinyl, phthalazinyl, pyridyl, pteridinyl, purinyl, quinazolinyl, quinoxalinyl, quinolinyl, isoquinolinyl, tetrazoyl, imidazolyl, tetrahydroisouinolyl, piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazinyl, pyrimidinyl, pyridazinyl, oxazolyl, oxazolinyl, oxasolidinyl, triazolyl, indanyl, isoxazolyl, isoxasolidinyl, morpholinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl, quinolyl, isoquinolyl, decahydroisoquinolyl, benzimidazolyl, thiadiazolyl, benzopyranyl, benzothiazolyl, benzooxazolyl, furyl, tetrahydrofurtyl, tetrahydropyranyl, thienyl, benzothienyl, thiamorpholinyl, thiamorpholinyl sulfoxide, thiamorpholinyl sulfone, dioxaphospholanyl, oxadiazolyl, chromanyl, isochromanyl and the like and mixtures thereof.

Representative examples of heteroaryl groups for use herein include, by way of example, a substituted or unsubstituted heterocyclic ring radical as defined above. The heteroaryl ring radical may be attached to the main structure at any heteroatom or carbon atom that results in the creation of a stable structure.

Representative examples of heteroarylalkyl groups for use herein include, by way of example, a substituted or unsubstituted heteroaryl ring radical as defined above directly bonded to an alkyl group as defined above. The heteroarylalkyl radical may be attached to the main structure at any carbon atom from the alkyl group that results in the creation of a stable structure.

Representative examples of heterocyclo groups for use herein include, by way of example, a substituted or unsubstituted heterocylic ring radical as defined above. The heterocyclo ring radical may be attached to the main structure at any heteroatom or carbon atom that results in the creation of a stable structure.

Representative examples of heterocycloalkyl groups for use herein include, by way of example, a substituted or unsubstituted heterocylic ring radical as defined above directly bonded to an alkyl group as defined above. The heterocycloalkyl radical may be attached to the main structure at carbon atom in the alkyl group that results in the creation of a stable structure.

Representative examples of a "polymerizable ethylenically unsaturated organic radical" include, by way of example, (meth)acrylate-containing radicals, (meth)acrylamide-containing radicals, vinylcarbonate-containing radicals, vinylcarbamate-containing radicals, styrene-containing radicals and the like. In one embodiment, a polymerizable ethylenically unsaturated organic radical can be represented by the general formula:

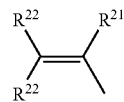

wherein $R^{21}$ is hydrogen, fluorine or methyl; $R^{22}$ is independently hydrogen, fluorine, an alkyl radical having 1 to 6 carbon atoms, or a —CO—Y—$R^{24}$ radical wherein Y is —O—, —S— or —NH— and $R^{24}$ is a divalent alkylene radical having 1 to about 10 carbon atoms.

The substituents in the 'substituted alkyl', 'substituted alkoxy', 'substituted cycloalkyl', 'substituted cycloalkylalkyl', 'substituted cycloalkenyl', 'substituted arylalkyl', 'substituted aryl', 'substituted heterocyclic ring', 'substituted heteroaryl ring,' 'substituted heteroarylalkyl', 'substituted heterocycloalkyl ring', 'substituted cyclic ring' and 'substituted carboxylic acid derivative' may be the same or different and include one or more substituents such as hydrogen, hydroxy, halogen, carboxyl, cyano, nitro, oxo (=O), thio (=S), substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkenyl, substituted or unsubstituted amino, substituted or unsubstituted aryl, substituted or unsubstituted heteroaryl, substituted heterocycloalkyl ring, substituted or unsubstituted heteroarylalkyl, substituted or unsubstituted heterocyclic ring, substituted or unsubstituted guanidine, —COORx, —C(O)Rx, —C(S)Rx, —C(O)NRxRy, —C(O)ONRxRy, —NRxCONRyRz, —N(Rx)SORy, —N(Rx)SO2Ry, —(=N—N(Rx)Ry), —NRxC(O)ORy, —NRxRy, —NRxC(O)Ry-, —NRxC(S)Ry-NRxC(S)NRyRz, —SONRxRy-, —SO2NRxRy-, —ORx, —ORxC(O)NRyRz, —ORxC(O) ORy-, —OC(O)Rx, —OC(O)NRxRy, —RxNRyC(O)Rz, —RxORy, —RxC(O)ORy, —RxC(O)NRyRz, —RxC(O) Rx, —RxOC(O)Ry, —SRx, —SORx, —SO$_2$Rx, —ONO$_2$, wherein Rx, Ry and Rz in each of the above groups can be the same or different and can be a hydrogen atom, substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkenyl, substituted or unsubstituted amino, substituted or unsubstituted aryl, substituted or unsubstituted heteroaryl, 'substituted heterocycloalkyl ring' substituted or unsubstituted heteroarylalkyl, or a substituted or unsubstituted heterocyclic ring.

Monomers having the following structures are useful in forming medical devices:

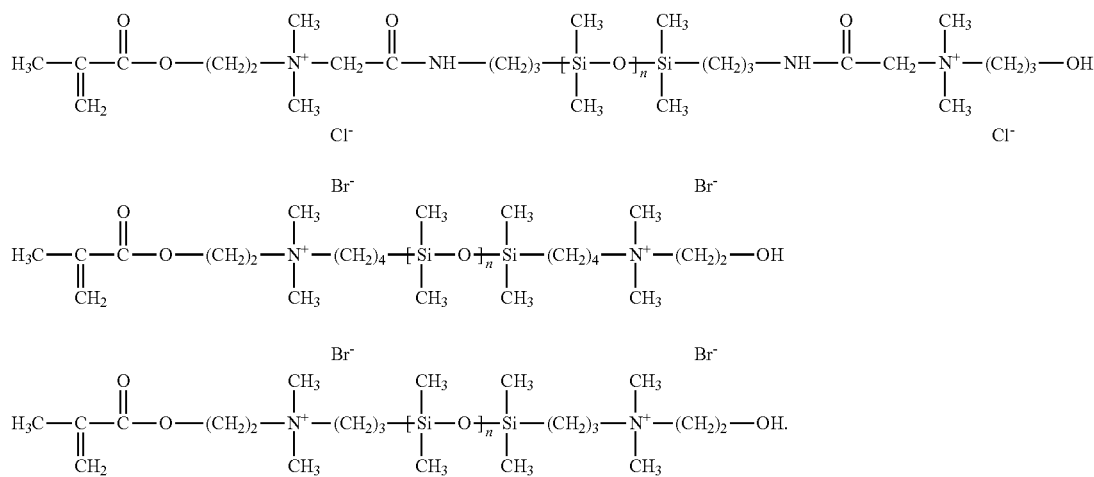

A schematic representation of a synthetic method for making the novel cationic silicon-containing monomers disclosed herein is provided below:

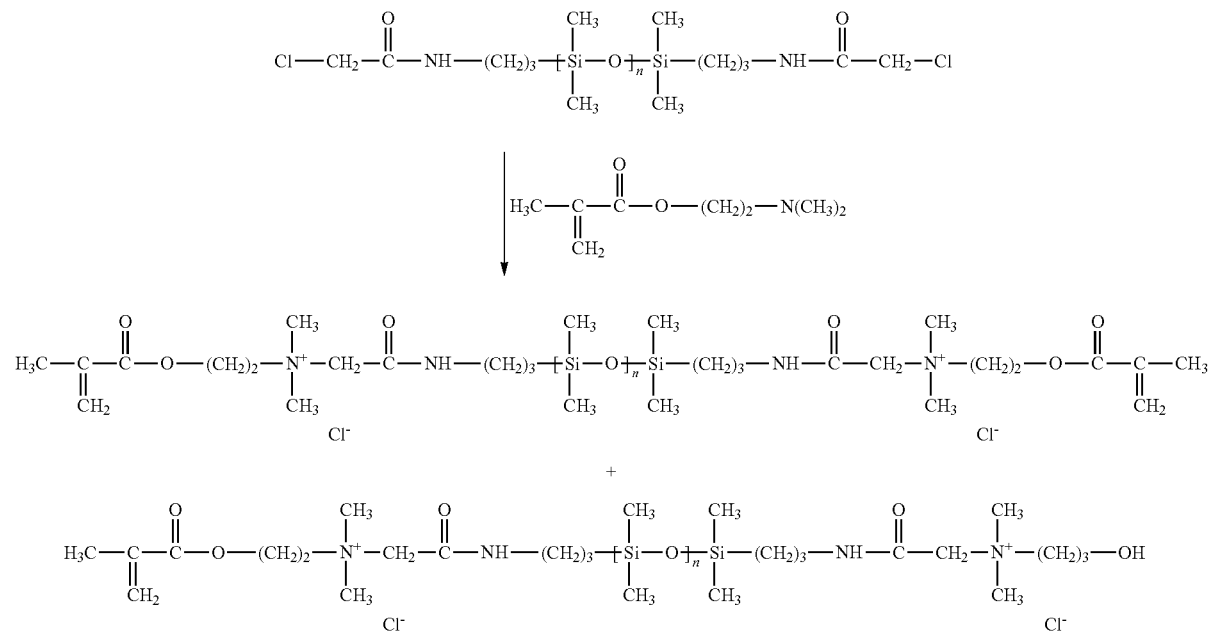

In a second aspect, the invention includes a reaction mixture comprising such mono vinyl polymerizable dicationic siloxanes which are easily synthesized to afford a predictable mixture of mono-vinyl and di-vinyl groups to provide a controlled reduction in the cross-link density of the resulting polymerized device. It is noted that a certain amount of non-vinyl containing polymer is also obtained, but can be minimized via appropriate stoichiometry to an acceptable amount. The resulting mixture comprises Di-polymerizable (Cross-Linking)

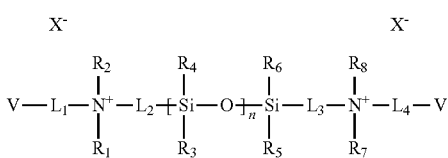

Mono-polymerizable (Non-Cross-Linking)

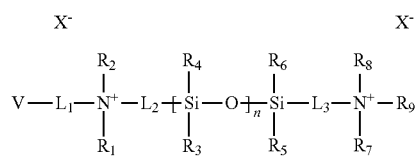

wherein $L_1$, $L_2$, $L_3$, $R_1$, $R_2$, $R_3$, $R_4$, $R_5$, $R_6$, $R_7$, $R_8$, $R_9$, n and $X^-$ are as s $L_4$ is independently the same or different as $L_1$, $L_2$ and $L_3$.

In a third aspect, the invention includes articles formed of device forming monomer mixes comprising the monomers of formula (I). According to preferred embodiments, the article is the polymerization product of a mixture comprising the aforementioned cationic monomer and at least a second monomer. Preferred articles are optically clear and useful as a contact lens.

A method of making articles comprising monomers of the invention herein comprises providing a monomer mixture comprising the monomer of claim 1 and at least a second monomer, subjecting the monomer mixture to polymerizing conditions to provide a polymerized device, extracting the polymerized device, and packaging and sterilizing the polymerized device.

Useful articles made with these materials may require hydrophobic, possibly silicon containing monomers. Preferred compositions have both hydrophilic and hydrophobic monomers. The invention is applicable to a wide variety of polymeric materials, either rigid or soft. Especially preferred polymeric materials are lenses including contact lenses, rigid gas permeable contact lenses, phakic and aphakic intraocular lenses and corneal implants although all polymeric materials including biomaterials are contemplated as being within the scope of this invention. Especially preferred are silicon containing hydrogels.

The present invention also provides medical devices such as heart valves and films, surgical devices, vessel substitutes, intrauterine devices, membranes, diaphragms, surgical implants, blood vessels, artificial ureters, artificial breast tissue and membranes intended to come into contact with body fluid outside of the body, e.g., membranes for kidney dialysis and heart/lung machines and the like, catheters, mouth guards, denture liners, ophthalmic devices, and especially contact lenses.

Silicon containing hydrogels are prepared by polymerizing a mixture containing at least one silicon containing monomer and at least one hydrophilic monomer. The silicon containing monomer may function as a crosslinking agent (a crosslinker being defined as a monomer having multiple polymerizable functionalities) or a separate crosslinker may be employed.

An early example of a silicon containing contact lens material is disclosed in U.S. Pat. No. 4,153,641 (Deichert et al assigned to Bausch & Lomb Incorporated). Lenses are made from poly(organosiloxane) monomers which are a, c terminally bonded through a divalent hydrocarbon group to a polymerized activated unsaturated group. Various hydrophobic silicon-containing prepolymers such as 1,3-bis(methacryloxyalkyl)polysiloxanes were copolymerized with known hydrophilic monomers such as 2-hydroxyethyl methacrylate (HEMA).

U.S. Pat. No. 5,358,995 (Lai et al) describes a silicon containing hydrogel which is comprised of an acrylic ester-capped polysiloxane prepolymer, polymerized with a bulky polysiloxanylalkyl (meth)acrylate monomer, and at least one hydrophilic monomer. Lai et al is assigned to Bausch & Lomb Incorporated and the entire disclosure is incorporated herein by reference. The acrylic ester-capped polysiloxane prepolymer, commonly known as $M_2 D_x$ consists of two acrylic ester end groups and "x" number of repeating dimethylsiloxane units. The preferred bulky polysiloxanylalkyl (meth)acrylate monomers are TRIS-type (methacryloxypropyl tris(trimethylsiloxy)silane) with the hydrophilic monomers being either acrylic- or vinyl-containing.

Other examples of silicon-containing monomer mixtures which may be used with this invention include the following: vinyl carbonate and vinyl carbamate monomer mixtures as disclosed in U.S. Pat. Nos. 5,070,215 and 5,610,252 (Bambury et al); fluorosilicon monomer mixtures as disclosed in U.S. Pat. Nos. 5,321,108; 5,387,662 and 5,539,016 (Kunzler et al); fumarate monomer mixtures as disclosed in U.S. Pat. Nos. 5,374,662; 5,420,324 and 5,496,871 (Lai et al) and urethane monomer mixtures as disclosed in U.S. Pat. Nos. 5,451,651; 5,648,515; 5,639,908 and 5,594,085(Lai et al), all of which are commonly assigned to assignee herein Bausch & Lomb Incorporated, and the entire disclosures of which are incorporated herein by reference.

Examples of non-silicon hydrophobic materials include alkyl acrylates and methacrylates.

As a non limiting example, the mono vinyl polymerizable dicationic siloxanes of the invention herein may be copolymerized with a wide variety of monomers to produce silicon hydrogel lenses. For example, a second monomer may be selected from unsaturated carboxylic acids; methacrylic acids, acrylic acids; acrylic substituted alcohols; 2-hydroxyethylmethacrylate, 2-hydroxyethylacrylate; vinyl lactams; N-vinyl pyrrolidone (NVP) N-vinyl caprolactone; acrylamides; methacrylamide, N,N-dimethylacrylamide; methacrylates; ethylene glycol dimethacrylate, methyl methacrylate, allyl methacrylate; hydrophilic vinyl carbonates, hydrophilic vinyl carbamate monomers; hydrophilic oxazolone monomers, 3-methacryloyloxypropyl tris(trimethylsiloxy)silane, ethylene glycol dimethacrylate (EGDMA), allyl methacrylate (AMA) and mixtures thereof.

Suitable hydrophilic monomers include: unsaturated carboxylic acids, such as methacrylic and acrylic acids; acrylic substituted alcohols, such as 2-hydroxyethylmethacrylate and 2-hydroxyethylacrylate; vinyl lactams, such as N-vinylpyrrolidone (NVP) and 1-vinylazonan-2-one; and acrylamides, such as methacrylamide and N,N-dimethylacrylamide (DMA).

Still further examples are the hydrophilic vinyl carbonate or vinyl carbamate monomers disclosed in U.S. Pat. No. 5,070,215, and the hydrophilic oxazolone monomers disclosed in U.S. Pat. No. 4,910,277. Other suitable hydrophilic monomers will be apparent to one skilled in the art.

Hydrophobic cross linkers would include methacrylates such as ethylene glycol dimethacrylate (EGDMA) and allyl methacrylate (AMA). In contrast to traditional silicon hydrogel monomer mixtures, the monomer mixtures containing, as an example, the mono vinyl polymerizable dicationic siloxanes of the invention herein are relatively water soluble. This feature provides advantages over traditional silicon hydrogel monomer mixtures in that there is less risk of incompatibility phase separation resulting in hazy lenses and the polymerized materials are extractable with water. However, when desired, traditional organic extraction methods may also be used. In addition, the extracted lenses demonstrate a good combination of oxygen permeability (Dk) and low modulus, properties known to be important to obtaining desirable contact lenses. Moreover, lenses prepared with the mono vinyl polymerizable dicationic siloxanes of the invention herein are wettable even without surface treatment, provide dry mold release, do not require solvents in the monomer mix (although solvents such as glycerol may be used), the extracted polymerized material is not cytotoxic and the surface is lubricious to the touch. In cases where the polymerized monomer mix containing the mono vinyl polymerizable dicationic siloxanes of the invention herein do not demonstrate a desirable tear strength, toughening agents such as TBE (4-t-butyl-2-hydroxycyclohexyl methacrylate) may be added to the monomer mix. Other strengthening agents are well known to those of ordinary skill in the art and may also be used when needed.

Although an advantage of the mono vinyl polymerizable dicationic siloxanes of the invention herein is that they are relatively water soluble and also soluble in their comonomers, an organic diluent may be included in the initial monomeric mixture. As used herein, the term "organic diluent" encompasses organic compounds which minimize incompatibility of the components in the initial monomeric mixture and are substantially nonreactive with the components in the initial mixture. Additionally, the organic diluent serves to minimize phase separation of polymerized products produced by polymerization of the monomeric mixture. Also, the organic diluent will generally be relatively non-inflammable.

Contemplated organic diluents include tert-butanol (TBA); diols, such as ethylene glycol and polyols, such as glycerol. Preferably, the organic diluent is sufficiently soluble in the extraction solvent to facilitate its removal from a cured article during the extraction step. Other suitable organic diluents would be apparent to a person of ordinary skill in the art.

The organic diluent is included in an amount effective to provide the desired effect. Generally, the diluent is included at 5 to 60% by weight of the monomeric mixture, with 10 to 50% by weight being especially preferred.

According to the present process, the monomeric mixture, comprising at least one hydrophilic monomer, at least one mono vinyl functionalized dicationic siloxanes and optionally the organic diluent, is shaped and cured by conventional methods such as static casting or spincasting.

Lens formation can be by free radical polymerization such as azobisisobutyronitrile (AIBN) and peroxide catalysts using initiators and under conditions such as those set forth in U.S. Pat. No. 3,808,179, incorporated herein by reference. Photo initiation of polymerization of the monomer mixture as is well known in the art may also be used in the process of forming an article as disclosed herein. Colorants and the like may be added prior to monomer polymerization.

Subsequently, a sufficient amount of unreacted monomer and, when present, organic diluent is removed from the cured article to improve the biocompatibility of the article. Release of non-polymerized monomers into the eye upon installation of a lens can cause irritation and other problems. Unlike other monomer mixtures that must be extracted with flammable solvents such as isopropyl alcohol, because of the properties of the novel mono vinyl polymerizable dicationic siloxanes of the invention herein, non-flammable solvents including water may be used for the extraction process.

Once the biomaterials formed from the polymerized monomer mix containing the mono vinyl polymerizable dicationic siloxanes disclosed herein are formed they are then extracted to prepare them for packaging and eventual use. Extraction is accomplished by exposing the polymerized materials to various solvents such as water, tert-butanol, etc. for varying periods of time. For example, one extraction process is to immerse the polymerized materials in water for about three minutes, remove the water and then immerse the polymerized materials in another aliquot of water for about three minutes, remove that aliquot of water and then autoclave the polymerized material in water or buffer solution.

Following extraction of unreacted monomers and any organic diluent, the shaped article, for example an RGP lens, is optionally machined by various processes known in the art. The machining step includes lathe cutting a lens surface, lathe cutting a lens edge, buffing a lens edge or polishing a lens edge or surface. The present process is particularly advantageous for processes wherein a lens surface is lathe cut, since machining of a lens surface is especially difficult when the surface is tacky or rubbery.

Generally, such machining processes are performed before the article is released from a mold part. After the machining operation, the lens can be released from the mold part and hydrated. Alternately, the article can be machined after removal from the mold part and then hydrated.

EXAMPLES

All solvents and reagents were obtained from Sigma-Aldrich, Milwaukee, Wis., and used as received with the exception of aminopropyl terminated poly(dimethylsiloxane), 900-

1000 and 3000 g/mol, obtained from Gelest, Inc., Morrisville, Pa., and methacryloxypropyltris(trimethylsiloxy)silane, obtained from Silar Laboratories, Scotia, N.Y., which were both used without further purification. The monomers 2-hydroxyethyl methacrylate and 1-vinyl-2-pyrrolidone were purified using standard techniques.

Analytical Measurements

NMR: $^1$H-Nuclear Magnetic Resonance (NMR) characterization was carried out using a 400 MHz Varian spectrometer using standard techniques in the art. Samples were dissolved in chloroform-d (99.8 atom % D), unless otherwise noted. Chemical shifts were determined by assigning the residual chloroform peak at 7.25 ppm. Peak areas and proton ratios were determined by integration of baseline separated peaks. Splitting patterns (s=singlet, d=doublet, t=triplet, q=quartet, m=multiplet, br=broad) and coupling constants (J/Hz) are reported when present and clearly distinguishable.

SEC: Size Exclusion Chromatography (SEC) analyses were carried out by injection of 100 µL of sample dissolved in tetrahydrofuran (THF) (5-20 mg/mL) onto a Polymer Labs PL Gel Mixed Bed E (x2) column at 35° C. using a Waters 515 HPLC pump and HPLC grade THF mobile phase flow rate of 1.0 mL/min, and detected by a Waters 410 Differential Refractometer at 35° C. Values of $M_n$, $M_w$, and polydispersity (PD) were determined by comparison to Polymer Lab Polystyrene narrow standards.

ESI-TOF MS. The electrospray (ESI) time of flight (TOF) MS analysis was performed on an Applied Biosystems Mariner instrument. The instrument operated in positive ion mode. The instrument was mass calibrated with a standard solution containing lysine, angiotensinogen, bradykinin (fragment 1-5) and des-Pro bradykinin. This mixture provides a seven-point calibration from 147 to 921 m/z. The applied voltage parameters were optimized from signal obtained from the same standard solution.

Stock solutions of the polymer samples were prepared as 1 mg/mL in tetrahydrofuran (THF). From these stock solutions, samples were prepared for ESI-TOF MS analysis as 30 µM solutions in isopropanol (IPA) with the addition of 2% by volume saturated NaCl in IPA. Samples were directly infused into the ESI-TOF MS instrument at a rate of 35 µL/min.

Mechanical properties and Oxygen Permeability: Modulus and elongation tests were conducted according to ASTM D-1708a, employing an Instron (Model 4502) instrument where the hydrogel film sample is immersed in borate buffered saline; an appropriate size of the film sample is gauge length 22 mm and width 4.75 mm, where the sample further has ends forming a dog bone shape to accommodate gripping of the sample with clamps of the Instron instrument, and a thickness of 200+50 microns.

Oxygen permeability (also referred to as Dk) was determined by the following procedure. Other methods and/or instruments may be used as long as the oxygen permeability values obtained therefrom are equivalent to the described method. The oxygen permeability of silicone hydrogels is measured by the polarographic method (ANSI Z80.20-1998) using an O2 Permeometer Model 201T instrument (Createch, Albany, Calif. USA) having a probe containing a central, circular gold cathode at its end and a silver anode insulated from the cathode. Measurements are taken only on pre-inspected pinhole-free, flat silicone hydrogel film samples of three different center thicknesses ranging from 150 to 600 microns. Center thickness measurements of the film samples may be measured using a Rehder ET-1 electronic thickness gauge. Generally, the film samples have the shape of a circular disk. Measurements are taken with the film sample and probe immersed in a bath containing circulating phosphate buffered saline (PBS) equilibrated at 35° C.+/−0.2°. Prior to immersing the probe and film sample in the PBS bath, the film sample is placed and centered on the cathode premoistened with the equilibrated PBS, ensuring no air bubbles or excess PBS exists between the cathode and the film sample, and the film sample is then secured to the probe with a mounting cap, with the cathode portion of the probe contacting only the film sample. For silicone hydrogel films, it is frequently useful to employ a Teflon polymer membrane, e.g., having a circular disk shape, between the probe cathode and the film sample. In such cases, the Teflon membrane is first placed on the premoistened cathode, and then the film sample is placed on the Teflon membrane, ensuring no air bubbles or excess PBS exists beneath the Teflon membrane or film sample. Once measurements are collected, only data with correlation coefficient value (R2) of 0.97 or higher should be entered into the calculation of Dk value. At least two Dk measurements per thickness, and meeting R2 value, are obtained. Using known regression analyses, oxygen permeability (Dk) is calculated from the film samples having at least three different thicknesses. Any film samples hydrated with solutions other than PBS are first soaked in purified water and allowed to equilibrate for at least 24 hours, and then soaked in PHB and allowed to equilibrate for at least 12 hours. The instruments are regularly cleaned and regularly calibrated using RGP standards. Upper and lower limits are established by calculating a +/−8.8% of the Repository values established by William J. Benjamin, et al., The Oxygen Permeability of Reference Materials, Optom Vis Sci 7 (12s): 95 (1997), the disclosure of which is incorporated herein in its entirety:

| Material Name | Repository Values | Lower Limit | Upper Limit |
| --- | --- | --- | --- |
| Fluoroperm 30 | 26.2 | 24 | 29 |
| Menicon EX | 62.4 | 56 | 66 |
| Quantum II | 92.9 | 85 | 101 |

Abbreviations

NVP 1-Vinyl-2-pyrrolidone
TRIS Methacryloxypropyltris(trimethylsiloxy)silane
HEMA 2-Hydroxyethyl methacrylate
v-64 2,2'-Azobis(2-methylpropionitrile)

Unless otherwise specifically stated or made clear by its usage, all numbers used in the examples should be considered to be modified by the term "about" and to be weight percent.

Example 1

Synthesis of 3-(chloroacetylamido)propyl Terminated poly(dimethylsiloxane)

To a vigorously stirred biphasic mixture of a solution of 3-aminopropyl terminated poly(dimethylsiloxane) (97.7 g, 3000 g/mol) obtained from Gelest, Inc., Morrisville, Pa., in dichloromethane (350 mL) and NaOH$_{(aq)}$ (0.75 M, 150 mL)

at 0° C. was added a solution of chloroacetyl chloride (8 mL, 0.1 mol) in dichloromethane (50 mL) dropwise. Following a one hour reaction period at ambient temperature, the organic layer was separated and stirred 5 hours over silica gel (25 g) and $Na_2SO_4$ (25 g) and filtered. Solvents were removed at reduced pressure to afford the product as a colorless liquid (85 g, 83%): $^1$H NMR ($CDCl_3$, 400 MHz) δ 6.64 (br, 2 H), 4.05 (s, 4 H), 3.29 (q, J=7 Hz, 4 H), 1.60-1.52 (m, 4 H), 0.56-0.52 (m, 4 H), 0.06 (s, approximately 264 H); GPC: $M_w$ 3075 g/mol, PD 1.80. The mass spectrum of this sample indicated a mass distribution of singly charged oligomers having a repeat unit mass of 74 Da. This corresponds to the targeted dimethyl siloxane (C2H6SiO) repeat unit chemistry. The targeted end group nominal mass for this sample is 326 Da ($C_{12}H_{24}N_2O_2SiCl_2$) and the required sodium charge agent has a mass of 23 Da (Na). The mass peaks in the distribution for this sample correspond to a nominal mass sequence of (74×n+326+23) where n is the number of repeat units. There is a good match between the experimental and theoretical isotopic distribution patterns for the oligomers evaluated.

Example 2

Synthesis of Cationic Methacrylate Terminated poly(dimethylsiloxane)

To a solution of 3-(chloroacetylamido)propyl end-capped poly(dimethylsiloxane) (20.0 g) from example 1 in ethyl acetate (25 mL) was added 2-(dimethylamino)ethyl methacrylate (3.40 mL, 20.1 mmol) and the mixture was heated 80 hours at 60° C. under a nitrogen atmosphere in the dark. The resulting solution was stripped of solvent and/or reagent at reduced pressure affording the product (23.1 g) containing a residual amount of 2-(dimethylamino)ethyl methacrylate (<10 w/w %) that is easily quantified by $^1$H NMR analysis: $^1$H NMR ($CDCl_3$, 400 MHz) δ 9.23 (br, 2 H), 6.07 (s, 2 H), 5.60 (s, 2 H), 4.71 (s, 4 H), 4.65-4.63 (m, 4 H), 4.18 (br, 4 H)3.47 (s, 12 H), 3.19-3.13 (m, 4 H), 1.88 (s, 6 H), 1.53-1.49 (m, 4 H), 0.51-0.47 (m, 4 H), 0.01 (s, approximately 327 H). The mass spectrum of this sample indicated a mass distribution of doubly charged oligomers having a repeat unit mass of 37 Da. When deconvoluted this corresponds to a repeat unit mass of 74 Da (37 Da×2). This corresponds to the targeted dimethyl siloxane ($C_2H_6SiO$) repeat unit chemistry. The targeted end group nominal mass for this sample is 570 Da ($C_{28}H_{54}N_4O_6Si$). The end group chemistry contains two quaternary nitrogen atoms and thus no additional charge agent is required. The two quaternary nitrogen ($N^+$) atoms also explain the presence of the doubly charged mass peaks. The mass peaks in the distribution for this sample correspond to a nominal mass sequence of ((74/2)×n+570) where n is the number of repeat units. There is a good match between the experimental and theoretical isotopic distribution patterns for the oligomers evaluated.

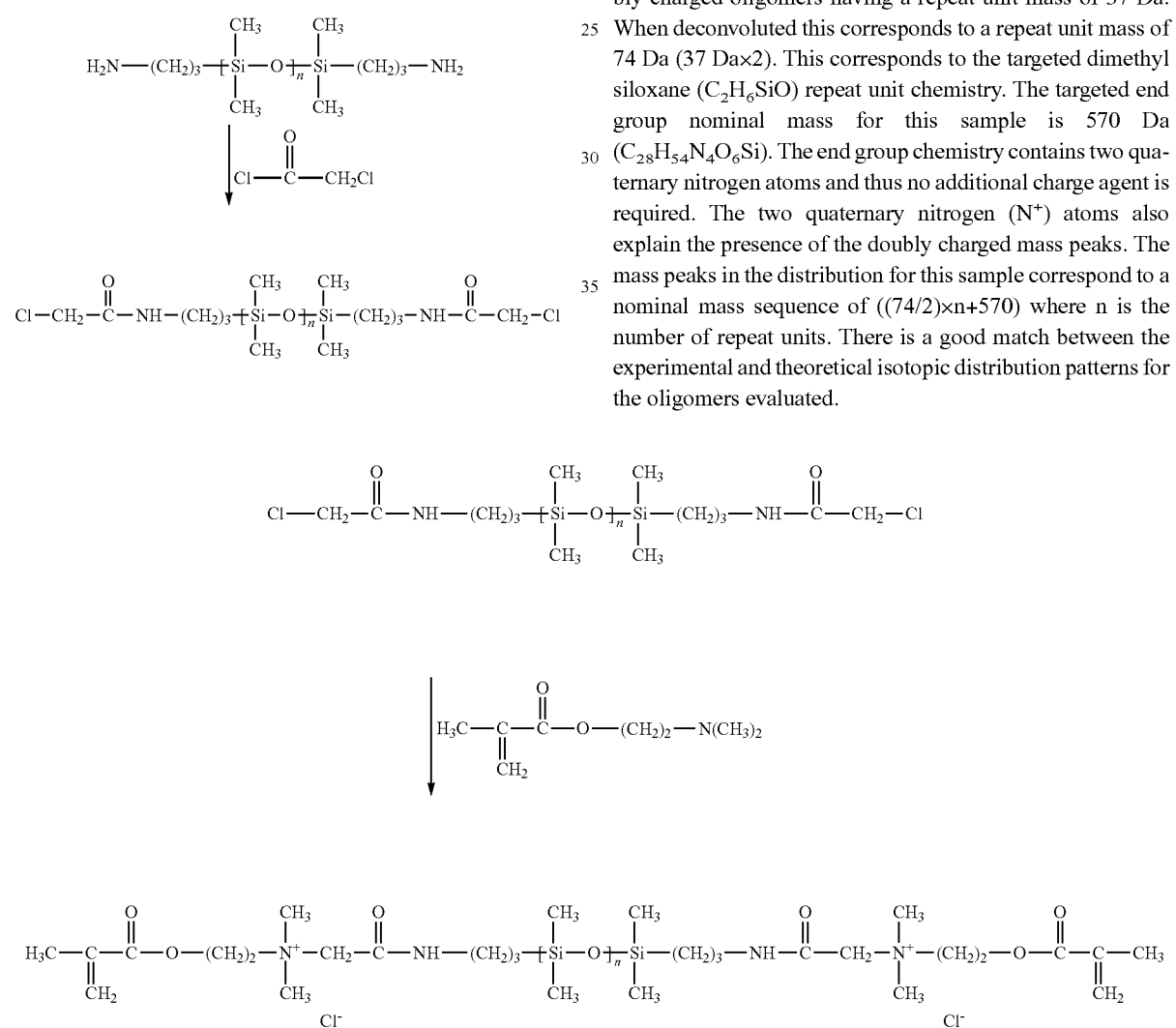

Example 3

Synthesis of Cationic Chloride Terminated poly(dimethylsiloxane) with Variable Terminal Methacrylate To a solution of 3-(chloroacetylamido)propyl end-capped poly(dimethylsiloxane) (50.0 g) from example 1 in ethyl acetate (50 mL) was added 2-(dimethylamino)ethyl methacrylate (3.03 mL, 18.0 mmol) and 3-(dimethylamino)propanol (0.71 mL, 6.1 mmol) and the mixture was heated 80 hours at 60° C. under a nitrogen atmosphere in the dark. The resulting solution was stripped of solvent and/or reagent at reduced pressure affording the product (53.5 g) containing a residual amount of 2-(dimethylamino)ethyl methacrylate and 3-(dimethylamino)propanol (<10 w/w %) that are easily quantified by $^1$H NMR analysis as described above.

Films were removed from glass plates and hydrated/extracted in deionized $H_2O$ for a minimum of 4 hours, transferred to fresh deionized $H_2O$ and autoclaved 30 min at 121° C. The cooled films were then analyzed for selected properties of interest in ophthalmic materials as describe in table 2. Mechanical tests were conducted in borate buffered saline according to ASTM D-1708a, discussed above.

TABLE 2

Properties of processed films containing cationic end-capped poly(dimethylsiloxane)

| Example | Modulus (g/mm$^2$)* |
|---------|---------------------|
| 3       | 210(21)             |
| 4       | 136(15)             |

*number in parentheses indicates standard deviation of final digit(s)

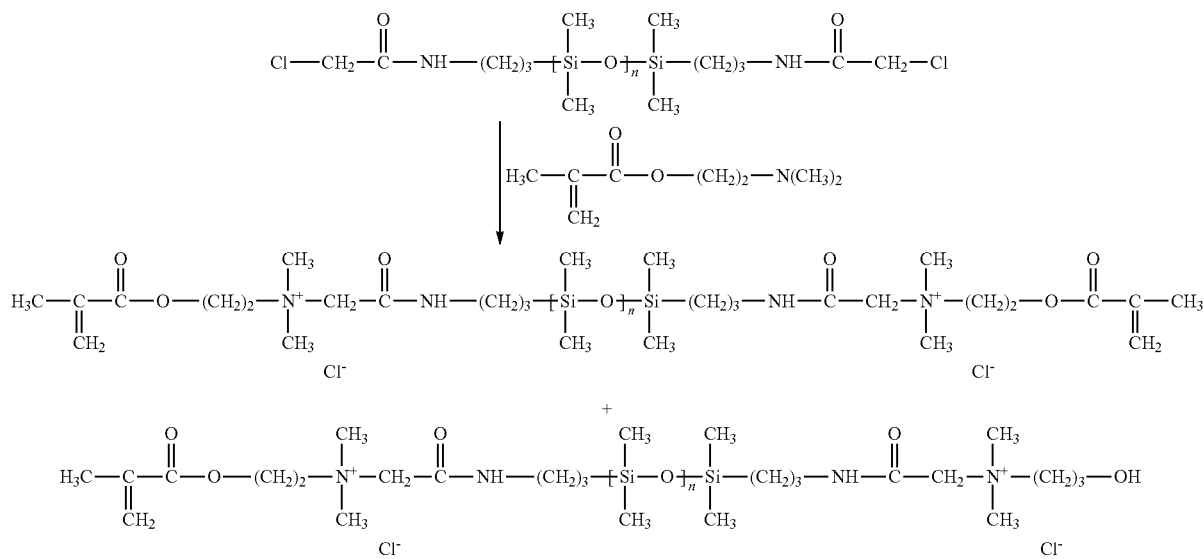

Example 4-5

Polymerization, Processing and Properties of Films Containing Cationic Siloxanyl Prepolymers Liquid monomer solutions containing cationic end-capped poly(dimethylsiloxane) prepolymers (from examples 2 and 3 above) as well as other monomers and initiator used commonly in ophthalmic materials were clamped between silanized glass plates at various thicknesses and polymerized using thermal decomposition of the free-radical generating additive by heating 2 h at 100° C. under a nitrogen atmosphere. Each of the formulations listed in table 1 afforded a transparent, tack-free, insoluble film.

TABLE 1

Formulations containing cationic end-capped poly(dimethylsiloxane)

| Ex. | Ex. 2 | Ex. 3 | NVP  | TRIS | v-64 |
|-----|-------|-------|------|------|------|
| 4   | 19.2  |       | 34.4 | 48.9 | 0.5  |
| 5   |       | 19.2  | 34.4 | 48.9 | 0.5  |

What is claimed is:

1. A monomer of formula (I)

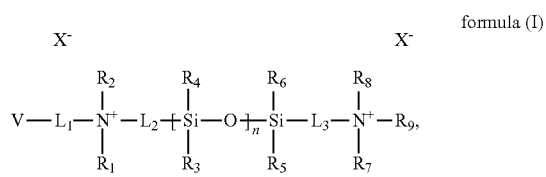

formula (I)

wherein $L_1$, $L_2$ and $L_3$ can individually be the same or different and are selected from the group consisting of urethanes, carbonates, carbamates, carboxyl ureidos, sulfonyls, a straight or branched C1-C30 alkyl group, a C1-C30 fluoroalkyl group, a C1-C20 ester group, an alkyl ether, cycloalkyl ether, cycloalkenyl ether, aryl ether, arylalkyl ether, a polyether containing group, an ureido group, an amide group, an amine group, a substituted or unsubstrtuted C1-C30 alkoxy group, a substituted or unsubstituted C3-C30 cycloalkyl group, a substituted or unsubstituted C3-C30 cycloalkylalkyl group, a substituted or unsubstituted C3-C30 cycloalkenyl group, a substituted or unsubstituted C5-C30 aryl group, a substituted or unsubstituted C5-C30 arylalkyl group, a substituted or unsubstituted C5-C30 heteroaryl group, a substituted or unsubstituted C3-C 30 heterocyclic ring, a substituted or unsubstituted C4-C30 heterocyclolalkyl group, a substituted or unsubstituted C6-C30 heteroarylalkyl group, a C5-C30 fluoroaryl group, or a hydroxyl substituted alkyl ether and combinations thereof; $X^-$ is at least a single charged counter ion, n is an integer from 1 to about 300; $R_1, R_2, R_3, R_4, R_5, R_6, R_7, R_8$ and $R_9$ are each independently hydrogen, a straight or branched C1-C30 alkyl group, a C1-C30 fluoroalkyl group, a C1-C20 ester group, an alkyl ether, cycloalkyl ether, cycloalkenyl ether, aryl ether, arylalkyl ether, a polyether containing group, an ureido group, an amide group, an amine group, a substituted or unsubstituted C1-C30 alkoxy group, a substituted or unsubstituted C3-C30 cycloalkyl group, a substituted or unsubstituted C3-C30 cycloalkylalkyl group, a substituted or unsubstituted C3-C30 cycloalkenyl group, a substituted or unsubstituted C5-C30 aryl group, a substituted or unsubstituted C5-C30 arylalkyl group, a substituted or unsubstituted C5-C30 heteroaryl group, a substituted or unsubstituted C3-C30 heterocyclic ring, a substituted or unsubstituted C4-C30 heterocyclolalkyl group, a substituted or unsubstituted C6-C30 heteroarylalkyl group, fluorine, a C5-C30 fluoroaryl group, or a hydroxyl group and V is a free radical polymerizable ethylenically unsaturated organic group.

2. The monomer of claim 1 wherein $X^-$ is selected from the group consisting of $Cl^-$, $Br^-$, $I^-$, $CF_3CO_2^-$, $CH_3CO_2^-$, $HCO_3^-$, $CH_3SO_4^-$, p-toluenesulfonate, $HSO_4^-$, $H_2PO_4^-$, $NO_3^-$, $CH_3CH(OH)CO_2^-$, $SO_4^{2-}$, $CO_3^{2-}$, $HPO_4^{2-}$ and mixtures thereof.

3. The monomer of claim 1 wherein $X^-$ is at least a single charged counter ion and is selected from the group consisting of $Cl^-$, $Br^-$, $I^-$, $CF_3CO_2^-$, $CH_3CO_2^-$, $HCO_3^-$, $CH_3SO_4^-$, p-toluenesulfonate, $HSO_4^-$, $H_2PO_4^-$, $NO_3^-$, and $CH_3CH(OH)CO_2^-$ and mixtures thereof.

4. The monomer of claim 1 having a structure selected from the group consisting of

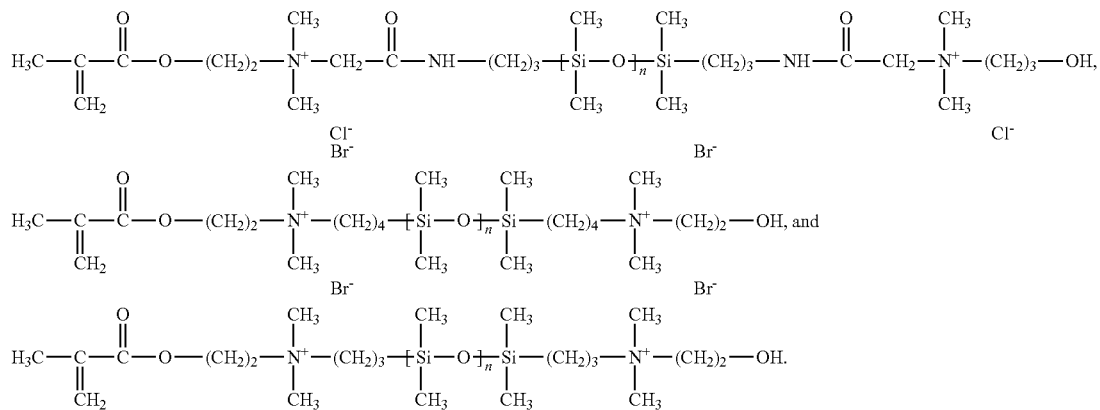

5. A monomer mix useful for making polymerized biomaterials comprising at least one monomer of claim 1 and at least one second monomer.

6. The monomer mix of claim 5, further comprising in addition to the second monomer a hydrophobic monomer and a hydrophilic monomer.

7. The monomer mix of claim 5 wherein the second monomer is selected from the group consisting of unsaturated carboxylic acids, acrylic substituted alcohols, vinyl lactams, acrylamides, methacrylates, hydrophilic vinyl carbonates, hydrophilic vinyl carbamate monomers, hydrophilic oxazolone monomers, and mixtures thereof.

8. A device comprising the monomer of claim 1 as a polymerized comonomer.

9. The device of claim 8 wherein the device is a contact lens.

10. The device of claim 9 wherein the contact lens is a rigid gas permeable contact lens.

11. The device of claim 9 wherein the contact lens is a soft contact lens.

12. The device of claim 9 wherein the contact lens is a hydrogel contact lens.

13. The device of claim 8 wherein the device is an intraocular lens.

14. The device of claim 13 wherein the intraocular lens is a phakic intraocular lens.

15. The device of claim 13 wherein the intraocular lens is an aphakic intraocular lens.

16. The device of claim 8 wherein the device is a conical implant.

17. The device of claim 8 wherein the device is selected from the group consisting of heart valves, intraocular lenses, films, surgical devices, vessel substitutes, intrauterine devices, membranes, diaphragms, surgical implants, blood vessels, artificial ureters, artificial breast tissue, membranes for kidney dialysis machines, membranes for heart/lung machines, catheters, mouth guards, denture liners, ophthalmic devices, and contact lenses.

18. A method of making a device comprising
providing a monomer mixture comprising the monomer of claim 1 and at least a second monomer;
subjecting the monomer mixture to polymerizing conditions to provide a polymerized device, and
extracting the polymerized device.

19. The method of claim 18 wherein the step of extracting is performed with non-flammable solvents.

20. The method of claim 18 wherein the step of extracting is performed with water.

21. The monomer mix of claim 5 wherein the second monomer is selected from the group consisting of methacrylic acid, acrylic acid, 2-hydroxyethylmethacrylate, 2-hydroxyethylacrylate, N-vinyl pyrrolidone (NVP), N-vinyl caprolactone, methacrylamide, N,N-dimethylacrylamide, ethylene glycol dimethacrylate, methyl methacrylate, allyl methacrylate, 3-methacryloyloxypropyl tris(trimethylsiloxy) silane and mixtures thereof.

22. The method of claim 18, further comprising the step of packaging and sterilizing the polymerized device.

* * * * *